United States Patent [19]
Reeves et al.

[11] Patent Number: 6,045,799
[45] Date of Patent: Apr. 4, 2000

[54] CHIMERIC CONTRACEPTIVE VACCINES

[75] Inventors: Jerry J. Reeves; Kevin P. Bertrand; Yuzhi Zhang, all of Pullman, Wash.

[73] Assignee: Washington State University, Pullman, Wash.

[21] Appl. No.: 09/072,508

[22] Filed: May 4, 1998

Related U.S. Application Data

[62] Division of application No. 08/897,527, Jul. 21, 1997.

[51] Int. Cl.[7] .......................... A61K 38/24; A61K 38/09; C07K 1/00

[52] U.S. Cl. .................................. 424/192.1; 424/198.1; 424/278.1; 530/328; 530/403; 530/367; 530/399

[58] Field of Search ............................. 424/192.1, 198.1, 424/278.1; 530/328, 403, 399, 367

[56] References Cited

PUBLICATIONS

Johnson, HE et al. J. Anim. Sci. 66(3):719–726, Mar. 1988.
Lowenadler, B et al. Molec. Immunol. 29(10):1185–1190, Oct. 1992.
Meloen, RH et al. Vaccine. 12(8):741–746, Aug. 1994.
Adams, T.E. et al., "Gonadotrope Function in Ovariectomized Ewes Actively Immunized against Gonadotropin–Releasing Hormone (GnRH)," *Biol. Reprod.*, 35:360–367 (1986).
Brown, B.W. et al., "Immunization of sheep against GnRH early in life: effects on reproductive function and hormones in ewes," *J. Reprod. Fertil.*, 103: 131–135 (1995).
Brown, B.W. et al., "Immunization of sheep against GnRH early in life: effects on reproductive function and hormones in rams," *J. Reprod. Fertil.*, 101:15–21 (1994).
Esbenshade, K.L. et al., "Active Immunization of Gilts against Gonadotropin releasing Hormone: Effects on Secretion of Gonadotropins–Reproductive Function, and Responses to Agonists of Gonadotropin–releasing Hormone," *Biol. Reprod.*, 33:569–577 (1985).
Garza, F., Jr. et al., "Active Immunization of Intact Mares against Gonadotropin–Releasing Hormone: Differential Effects on Secretion of Lutenizing Hormone and Follicle–Stimulating Hormone," *Biol. Reprod.*, 35:347–352 (1986).
Gottesman, S. et al., "Minimizing Proteolysis in *Escherichia coli*: Genetic Solutions," *Meth. Enzymol.* 185:119–129 (1990).
Hoskinson et al., "Vaxstrate: An Anti–reproductive Vaccine for Cattle," *Austral. J. Biotech.*, 4(3):166–176 (1990).
Humphries et al., "Molecular cloning of extensive sequences of the in vitro synthesized chicken ovalbumin structural gene," *Nucl. Acids Res.*, 4(7):2389–2406 (1977).
Jameson and Wolf, "The antigenic index: a novel algorithm for predicting antigenic determinants," CABIOS, 4(1):181–186 (1988).
Jameson, J.L. et al., "Human Follicle–Stimulating Hormone β–Subunit Gene Encodes Multiple Messenger Ribonucleic Acids," *Mol. Endocrinol.*, 2:806–815 (1988).

Kyte and Doolittle, "A Simple Method for Displaying the Hydropathic Character of a Protein," *J. Mol. Biol.*, 157:105–132 (1982).
Margalit et al., "Prediction of Immunodominant Helper T Cell Antigenic Sites From The Primary Sequence," *J. Immunol.*, 138:2213–2229 (1987).
Moore, J.T. et al., "Overcoming Inclusion Body Formation in a High–Level Expression System," *Prot. Expres. Purif.*, 4:160–163 (1993).
Mullis et al., "Specific Enzymatic Amplification of DNA in Vitro: The Polymerase Chain Reaction," *Cold Spring Harbor Symp. Quant. Biol.*, 51:263–273 (1986).
Prendiville, D.J. et al., "Immunization of Heifers Against Gonadotropin–Releasing Hormone: Antibody Titers, Ovarian Function, Body Growth, and Carcass Characteristics," *J. Anim. Sci.*, 73:2382–2389 (1995).
Rovan, E. et al., "Effect of active immunization to luteinizing–hormone–releasing hormone on the fertility and histoarchitecture of the reproductive organs of male rat," *Urol. Res.* 20:323–334 (1992).
Sanger, F. et al., "DNA sequencing with chain–terminating inhibitors," *Proc. Natl Acad Sci.*, (USA), 74(12):5463–5467 (1977).
Schanbacher, B. D., "Responses of ram lambs to active immunization against testosterone and luteinizing hormone–releasing hormone," Am. J. Physiol., 242:E201–E205 (1985).
Schweers, L. A. et al., "The Steroid–dependent Regulatory Element in the Ovalbumin Gene Does Not Function as a Typical Steroid Response Element," *J. Biol. Chem.*, 265(13):7590–7595 (1990).
Studier, F. W. et al., "Use of T7 RNA Polymerase to Direct Expression of Cloned Genes," *Meth. Enzymol.*, 185:60–89 (1990).
Talmadge, K. et al., "Evolution of the genes for the β subunits of human chorionic gonadotropin and luteinizing hormone," *Nature*, 307(5946):37–40 (1984).
Wetterman and Castree, "Immunization of heifers against gonadotropin releasing hormone delays puberty and causes the cessation of estrous cycles," *Anim. Reprod. Sci.*, 36:49–59 (1994).

*Primary Examiner*—David Saunders
*Assistant Examiner*—F. Pierre VanderVegt
*Attorney, Agent, or Firm*—Marshall, O'Toole, Gerstein, Murray & Borun

[57] ABSTRACT

The invention is directed to contraceptive vaccines comprising a carrier protein or fragment thereof in peptide linkage with a reproduction related polypeptide, protein or fragment thereof, and to DNAs encoding the chimeric proteins. The invention also includes the use of the chimeric proteins in immunocontraceptive methods.

4 Claims, 7 Drawing Sheets

FIGURE 7

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 42 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide NheI"

(xi) SEQUENCE DESCRIPTION: SEQ ID NO:1:

GGCAAGGCTG AACGAATAGC TAGCAACATC ATTTGGTTTG GT          42

(2) INFORMATION FOR SEQ ID NO:2:

(i) SEQUENCE CHARACTERISTICS:
        (A) LENGTH: 75 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide LHRH-3"

(xi) SEQUENCE DESCRIPTION: SEQ ID NO:2:

AAGTCTACTG GCAAGGCTGA ACGAATAGCT GCCTGGGCGC AGGCCGTAGG ACCAGTGCTG    60

AGCAACATCA TTTGG          75

(2) INFORMATION FOR SEQ ID NO:3:

(i) SEQUENCE CHARACTERISTICS:
        (A) LENGTH: 60 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide LHRH-4"

(xi) SEQUENCE DESCRIPTION: SEQ ID NO:3:

AATACTGTCG CCGAAGCCCG GCCGCAGGCC GTAGGACCAG TGCTGTCCTG GAAGTTTATC    60

(2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide LHRH-5"

(xi) SEQUENCE DESCRIPTION: SEQ ID NO:4:

```
GAGGACTTTG AGCTCGCCCG GCCGCAGGCC GTAGGACCAG TGCTGTGGAT CCGAATTAAT        60
```

(2) INFORMATION FOR SEQ ID NO:5:

(i) SEQUENCE CHARACTERISTICS:
        (A) LENGTH: 67 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide LHRH-6"

(xi) SEQUENCE DESCRIPTION: SEQ ID NO:5:

```
TATGCAGCAT TGGTCTTACG GTCTGCGCCC AGGCCAACAC TGGAGCTATG GCCTCCGTCC        60

GGGTGCG                                                                 67
```

(2) INFORMATION FOR SEQ ID NO:6:

(i) SEQUENCE CHARACTERISTICS:
        (A) LENGTH: 69 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide LHRH-7"

(xi) SEQUENCE DESCRIPTION: SEQ ID NO:6:

```
GATCCGCACC CGGACGGAGG CCATAGCTCC AGTGTTGGCC TGGGCGCAGA CCGTAAGACC        60

AATGCTGCA                                                               69
```

(2) INFORMATION FOR SEQ ID NO:7:

(i) SEQUENCE CHARACTERISTICS:
        (A) LENGTH: 65 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Oligonucleotide LHRH-8"

(xi) SEQUENCE DESCRIPTION: SEQ ID NO:7:

```
AGGTTCAGCA CTGGTCCTAT GGTTTACGCC CGGGCCAACA TTGGAGCTAC GGCCTGCGTC        60

CAGGT                                                                   65
```

(2) INFORMATION FOR SEQ ID NO:8:

(i) SEQUENCE CHARACTERISTICS:
        (A) LENGTH: 66 base pairs
        (B) TYPE: nucleic acid
        (C) STRANDEDNESS: single
        (D) TOPOLOGY: linear -continued (ii) MOLECULE TYPE: other nucleic acid
    (A) DESCRIPTION: /desc = "Oligonucleotide LHRH-9"

(xi) SEQUENCE DESCRIPTION: SEQ ID NO:8:

TCGAGACCTG GACGCAGGCC GTAGCTCCAA TGTTGGCCCG GGCGTAAACC ATAGGACCAG        60

TGCTGA        66

CHIMERIC CONTRACEPTIVE VACCINES

This is a divisional of U.S. application Ser. No. 08/897,527, filed Jul. 21, 1997, from which priority is claimed.

GRANT SUPPORT

The work described herein was supported in part by USDA grant no. 9401624. The government may retain certain rights in the invention.

BACKGROUND OF THE INVENTION

Fertility management in mammals is a global issue of agricultural, economic and social importance. Conventional approaches of preventing pregnancy are surgical, can cause morbidity and mortality, and are unacceptable in some countries. Other approaches to contraception include the use of various hormones to regulate the ovulatory cycle and which may be associated with certain side effects. Still other approaches to contraception include the use of zona pellucida proteins as immunocontraceptives to induce permanent or transient infertility.

The decapeptide luteinizing hormone releasing hormone (LHRH) is the key regulatory brain peptide that controls reproduction in mammals and, thus, is a logical target for devising approaches to contraception. The endocrine effects of active immunization against LHRH have been studied in a variety of young and adult male and female animals (Adams et al., *Biol. Reprod.* 35:360, (1986); Esbenshade et al., *Biol. Reprod.* 33:569, (1985); Garza et al., *Biol. Reprod.* 35:347, (1986); Johnson et al., *J. Anim. Sci.* 66:719, (1988); Schanbacher et al., *Am. J. Physiol.* 242:3201, (1985)). These studies demonstrated decreases in gonadotropins, sperm production, follicular development, ovulation and conception after immunization against LHRH chemically conjugated to a carrier protein.

Johnson et al., *J. Anim. Sci.* 66:719, (1988) developed a conjugated ovalbumin LHRH molecule which, when used with Complete Preund's Adjuvant (CFA), was 100% effective in preventing pregnancy in a limited number of animals. However, in a commercial application in Australia, LHRH conjugated to ovalbumin (Vaxtrate) prevents only 80% of pregnancies of heifers (Hoskinson et al., *Austral. J. Biotech.* 4:166–176 (1990)).

Although immunoneutralization of LHRH by a chemically conjugated vaccine could provide a safe, humane and effective approach to preventing reproduction, such vaccines face considerable obstacles to approval for use in the United States. Such obstacles arise from the fact that chemical conjugation does not produce an antigen with a homogenous known structure within and between batches. Therefore, there remains a need for a vaccine directed to reproduction related polypeptides such as the hypothalamic hormone LHRH and the pituitary gonadotropins luteinizing hormone (LH) and follicle stimulating hormone (FSH), which vaccines have known reproducible structures.

SUMMARY OF THE INVENTION

The present invention is directed to chimeric proteins comprising a carrier protein or a polypeptide fragment thereof and a reproduction related polypeptide or fragment thereof. Preferred reproduction related polypeptides include LHRH, LH and FSH.

In another aspect of the invention, the chimeric polypeptide comprises a carrier protein or fragment thereof and two or more different reproduction related polypeptides or proteins.

In a preferred embodiment of the present invention, the carrier protein is ovalbumin, although other proteins such as thioredoxin or others may be used as a carrier. Preferred reproduction related hormones are follicle stimulating hormone (FSH) and luteinizing hormone (LH). More preferred is the hypothalamic hormone luteinizing hormone releasing hormone (LHRH) which controls synthesis and release of both pituitary gonadotropins LH and FSH. In another preferred embodiment the chimeric protein of the present invention comprises an ovalbumin carrier protein having an insertion of one or more full length LHRH molecules. Preferably, LHRH is inserted into potentially antigenic regions of the ovalbumin carrier protein. Such antigenic regions may be B-cell epitopes, helper T-cell antigenic epitope sites, and sites having surface exposure.

Also contemplated by the invention are chimeric proteins comprising a carrier protein or fragment thereof and one or more fragments of a reproduction related protein hormone such as LHRH, LH or FSH LHRH for use as an immunocontraceptive vaccine.

Another aspect of the invention is directed to immunocontraceptive methods which comprise administering to a mammal, including humans, an immunocontraceptively effective dose of a chimeric protein according to the present invention. The chimeric protein of the present invention may be administered with a suitable diluent, adjuvant, carrier or in a depot (slow release) formulation to allow prolonged exposure of the chimeric protein to the host mammal's immune system.

Also contemplated by the present invention are nucleic acids encoding the chimeric proteins of the present invention. Vectors comprising nucleic acids of the present invention are also within the scope of the invention. Such vectors include, but are not limited to, plasmids, phage, animal viruses such as vaccinia virus, adenovirus, herpesviruses, retroviruses, insect viruses such as baculoviruses, and others. Host cells transformed with the vectors of the present invention are also within the scope of the invention. Host cells are selected in part based on the vector to be used for expression of the chimeric polypeptide of the invention. Suitable host cells include, but are not limited to, prokaryotic cells such as *E. coli* and other bacteria, eukaryotic cells such as yeast, (e.g., *Pichia pastoris*), insect cells, mammalian cells (e.g., CHO cells, HeLa cells).

The invention is further directed to methods for producing antibodies in mammals the antibodies being directed to reproduction related polypeptides such as LHRH, LH and FSH. Generally, the method comprises administering to a mammal an immunologically effective dose of a chimeric polypeptide according to the present invention. The chimeric polypeptide may be combined with an adjuvant in order to improve the host animal's immune response to the polypeptide. Appropriate dosages and routes of administration are readily determined by those of ordinary skill in the art.

The invention is also directed to pharmaceutical composition comprising a chimeric polypeptide according to the present invention and pharmaceutically acceptable diluents, adjuvants, excipients or carriers.

BRIEF DESCRIPTION OF THE DRAWINGS

FIG. 1 depicts the structure of plasmid pOV.

FIG. 2 shows schematic structures of recombinant ovalbumin, ovalbumin-LHRH-4 and ovalbumin-LHRH-7 sequences produced from pET plasmid derivatives.

FIG. 3 illustrates expression of recombinant ovalbumin, ovalbumin-LHRH-4 and ovalbumin-LHRH-7 from plasmids pYZ24, pYZ24-5 and pYZ24-6, respectively.

DETAILED DESCRIPTION

The present invention is directed to chimeric proteins useful for immunocontraception. The chimeric proteins of the present invention comprise a carrier proteins or a fragment thereof which maintains potential antigenic sites or which is capable of giving rise to an antigenic site and at least one reproduction related polypeptide such as luteinizing hormone releasing hormone (LHRH) and/or luteinizing hormone (LH) or follicle stimulating hormone (FSH) or a fragment or fragments thereof.

A preferred embodiment of the present invention is directed to a chimeric protein comprising ovalbumin and at least one full length LHRH decapeptide although the number and position of the LHRH polypeptides may vary. The chimeric proteins of the present invention comprise the carrier protein in peptide linkage with the reproduction related polypeptide.

Previous studies (Esbenshade et al., *Biol. Reprod.* 33:569 (1985); Schanbacher et al., *Am. J. Physiol.* 242:3201 (1985); Adams et al., *Biol. Reprod.* 35:360 (1986); Garza et al., *Biol. Reprod.* 35:347 (1986); Johnson et al., *J. Anim. Sci.* 66:719 (1988); Hoskinson et al., *Austral. J. Biotech.* 4:166–176 (1990); Adams et al., *Biol. Reprod.* 35:360 (1992); Rovan et al., *Urol. Res.* 20:323–334 (1992); Brown et al., *J. Reprod. Fertil.* 101:15–21 (1994); Meloen et al., *Vaccine* 12:741–747 (1994); Wettermann et al., *Anim. Reprod. Sci.* 36:49–59 (1994); Brown et al., *J. Reprod. Fertil.* 101:131–135 (1995); Prendiville et al., *J. Anim. Sci.* 73:2382–2389 (1995)) of LHRH directed vaccines involved the use of LHRH chemically conjugated to carrier proteins. Meloen et al., *Vaccine* 12:741–747 (1994) reported that LHRH conjugated as a tandem molecule was much more immunogenic than LHRH monomer conjugated to a carrier protein. However, as described above, such conjugated vaccines suffer the disadvantage of lacking homogenous and known structures that are consistent within and between batches. In a preferred embodiment, the present invention is directed to a genetically engineered LHRH vaccine which has a known and consistent structure. As is described in more detail below, chimeric polypeptides comprising one or more LHRH polypeptides inserted in ovalbumin carrier proteins by way of a peptide linkage were capable of inducing anti-LHRH antibodies and to render treated animal infertile.

Other embodiments of the invention encompass chimeric proteins which comprise other reproduction related polypeptides or fragments thereof including FSH or LH. (See Jameson, et al., *Mol. Endocrinol* 2:806–815 (1988)(FSH), and Talmadge, et al., Nature 307 (5946):37–40 (1984) (LH), both of which are incorporated herein by reference).

The following examples describe chimeric polypeptides having from one to seven LHRH inserts in an ovalbumin carrier protein. Chimeric proteins having four and seven LHRH inserts were shown to be capable of inducing anti-LHRH antibodies, with the chimeric protein having seven LHRH inserts (ovalbumin-LHRH-7) inducing the highest level antibody titer, which was accompanied by a significant decrease in uterine weight, an indicator of diminished reproductive ability. While four of five mice treated with the chimeric protein having four LHRH inserts (ovalbumin-LHRH-4 group) had a titer against LHRH, there was no observable decrease in uterine-ovarian weight.

In view of the guidance provided in the present application, one of ordinary skill in the art would, using routine methods, be able to determine the optimum number of reproduction related polypeptide inserts in a carrier protein to obtain the desired biological effects. Optimization of the dosages and routes of administration of a chimeric protein of the invention is also a matter of routine.

The following Examples are presented by way of illustration and are in no way intended to limit the scope of the invention as set out in the appended claims.

Example 1 describes the construction of plasmids encoding chimeric ovalbumin-LHRH proteins.

Example 2 describes the solubility and purification of chimeric ovalbumin-LHRH proteins.

Example 3 describes the vaccination of mice with chimeric ovalbumin-LHRH proteins.

Example 4 describes the vaccination of mice with chimeric ovalbumin-LHRH proteins and various adjuvants.

Example 5 describes the vaccination of heifers with chimeric ovalbumin-LHRH protein.

EXAMPLE 1

Construction of Plasmids Encoding Chimeric Ovalbumin-LHRH Polypeptides

Preferably, the chimeric polypeptides of the present invention are designed so as to insert the reproduction related polypeptide (or fragment thereof) against which immunization is sought via peptide linkage into regions of the carrier protein or polypeptide fragment thereof which correspond to potential antigenic sites on the carrier, although other sites are contemplated by the invention. It is also recognized that insertion of a reproduction related polypeptide into a carrier protein at any site may create additional antigenic sites or alter existing antigenic sites.

Potential antigenic sites into which the reproduction related polypeptides are to be inserted may be identified by the use of computer programs such as programs AMPHI (Margalit et al., *J. Immunol.* 138:2213–2229 (1987)) and PLOTSTRUCTURE (Jameson et al., *CABIOS* 4:181–186 (1988); Kyte et al., *J. Mol. Biol.* 157:105–132 (1982)) in the Genetics Computer Group (GCG) Software package which were used to predict potential B-cell and helper T-cell antigenic sites, surface exposure and accessibility of recombinant proteins. Using these programs, two potential antigenic regions in ovalbumin were identified corresponding to a region between amino acids 51–73 and a region between amino acids 81–99. (See eg., Humphries et al., *Nucl. Acids Res.*, 4:2389–2406 (1977) disclosing ovalbumin cDNA sequence and incorporated herein by reference.) These two sites were chosen for LHRH insertion. Other sites near the N-terminus and C-terminus of ovalbumin were also chosen for insertion of LHRH in view of their high probability of surface exposure. According to the predicted surface exposure, flexibility, accessibility and antigenic index based on the amino acid sequence, ovalbumin-LHRH-7 should be more antigenic than ovalbumin-LHRH-4 in stimulating the production of anti-LHRH antibodies.

Plasmids encoding ovalbumin-LHRH chimeras were prepared as described below using the oligonucleotides set out in Table 1.

acid 18–381 with one LHRH insertion were obtained. Derivatives of pET22b containing the ovalbumin fragment

TABLE 1

Oligonucleotides Used for Oligonucleotide-Directed Mutagenesis and Cassette Mutagenesis

| Oligo-nucleotide | Sequence[a,b] | Purpose |
|---|---|---|
| NheI | 3' TGG TTT GGT TTA CTA CAA <u>CGA TCG</u> ATA AGC AAG TCG GAA CGG 5' (SEQ ID NO: 1) | Insert NheI site between aa97 & 98 of ovalbumin |
| LHRH-3 | 3' GGT TTA CTA CAA CGA <u>GTC GTG ACC AGG ATG CCG GAC GCG GGT CCG</u> TCG ATA AGC AAG TCG GAA CGG TCA TCT GAA 5' (SEQ ID NO: 2) | Insert LHRH into NheI site |
| LHRH-4 | 3' CTA TTT GAA GGT CCT <u>GTC GTG ACC AGG ATG CCG GAC GCC GGC CCG</u> AAG CCG CTG TCA TAA 5' (SEQ ID NO: 3) | Insert LHRH into Site 2 |
| LHRH-5 | 3' TAA TTA AGC CTA GGT <u>GTC GTG ACC AGG ATG CCG GAC GCC GGC CCG</u> CTC GAG TTT CAG GAG 5' (SEQ ID NO: 4) | Insert LHRH into Site 1 |
| LHRH-6 | 5' T ATG <u>CAG CAT TGG TCT TAC GGT CTG CGC CCA GGC CAA CAC TGG AGC TAT GGC CTC CGT CCG GGT GCG</u> 3' (SEQ ID NO: 5) | Insert tandem LHRH into Site 4 |
| LHRH-7 | 3' AC <u>GTC GTA ACC AGA ATG CCA GAC GCG GGT CCG GTT GTG ACC TCG ATA CCG GAG GCA GGC CCA</u> CGC CTA G 5' (SEQ ID NO: 6) | |
| LHRH-8 | 5' AG GTT <u>CAG CAC TGG TCC TAT GGT TTA CGC CCG GGC CAA CAT TGG AGC TAC GGC CTG CGT CCA GGT</u> C 3' (SEQ ID NO: 7) | Insert tandem LHRH LHRH into Site 5 |
| LHRH-9 | 3' A <u>GTC GTG ACC AGG ATA CCA AAT GCG GGC CCG GTT GTA ACC TCG ATG CCG GAC GCA GGT CCA GAG CT</u> 5' (SEQ ID NO: 8) | |

[a]Relevant features of sequences are underlined.
[b] Sequences of oligonucleotides from 5' to 3' and from 3' to 5' are coding strand and template strand, respectively.

Figure 1:
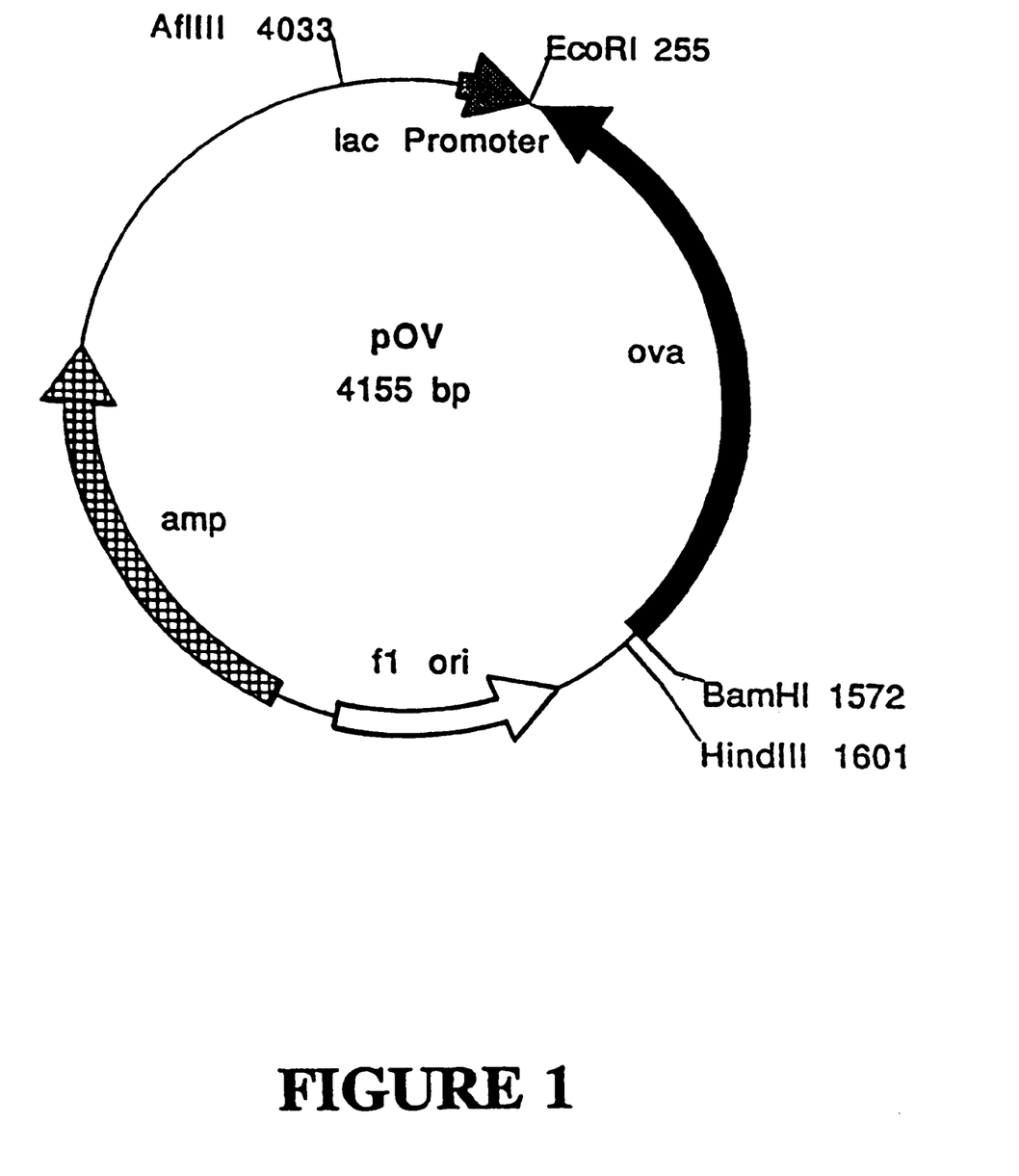

Plasmid pOV shown in FIG. 1 (and alternatively referred to as pOV1), a pTZ18R derivative containing ovalbumin cDNA corresponding to amino acids 7 to 386, is described in Schweers et al., *J. Biol. Chem.*, 265:7590–7595 (1990) incorporated herein by reference. A cDNA sequence encoding ovalbumin is set out in Humphries et al., *Nucl. Acids Res.*, 4:2389–2406 (1977) and is incorporated herein by reference. To express ovalbumin in *E. coli*, the orientation of the ovalbumin cDNA insert in pOV was reversed by subcloning the BamHI-EcoRI fragment from pOV into pTZ19U (BioRad Laboratories, Hercules, Calif.). The resulting plasmid was designated pOVR.

A NheI site was then inserted into pOVR after amino acid 97 of ovalbumin (site 3) by oligonucleotide-directed mutagenesis (Table 1) using the reagents and protocol from the Muta-Gene kit (BioRad Laboratories, Hercules, Calif.). The plasmid containing the NheI site was designated pNheI. An LHRH DNA sequence (Table 1) was inserted into the NheI site of pNheI to form plasmid pLHRH.

Because preliminary studies showed that proteins expressed from the lac promoter of pOVR and pLHRH were produced at relatively low levels, the ovalbumin and hybrid ovalbumin-LHRH genes were subcloned from pOVR and pLHRH into pET22b (Novagen, Madison, Wis.), an expression vector containing the strong phage T7 transcription and translation initiation signals. The Polymerase Chain Reaction (PCR) (Mullis et al., Cold Spring Harbor *Symp. Quant. Biol.* 51:263–273 (1986)) was used to generate an ovalbumin fragment suitable for cloning into pET22b. The primers were designed to incorporate a BamHI site at the 5' end of the fragment and a HindIII site at the 3' end. PCR products corresponding to amino acid 18–381 of ovalbumin or amino or ovalbumin fragment with one LHRH insert were designated pETOVA and pETLHRH-1, respectively.

To insert LHRH DNA before amino acid 18 and between amino acid 65 and amino acid 66 of ovalbumin, additional rounds of oligonucleotide-directed mutagenesis were conducted using pETLHRH-1 as a template. A plasmid containing the ovalbumin fragment with 3 LHRH inserts was designated pETLHRH-4. Regions of DNA spanning the NheI site in pNheI and the LHRH insertions in pLHRH and pETLHRH-4 were sequenced using the Sanger dideoxy method (Sanger, *Proc. Natl. Acad. Sci.* (USA) 74:5463–5467 (1977); Sequence version 2.0, United Stated Biochemicals) to confirm the plasmid sequences.

To increase the plasmid stability and thereby increase expression efficiency, the ovalbumin DNA fragment from pETOVA and the ovalbumin DNA fragment with 3 LHRH inserts from pETLHRH-4 were subcloned as BamHI-HindIII fragments into pET24b (Novagen) to form pYZ24 and pYZ24–4, respectively. pET24b carries a kanamycin-resistance gene and is more stable than pET22b which carries an ampicillin resistance gene.

Plasmid pYZ24 was digested with BamHI and NdeI and then ligated to a double-stranded tandem LHRH DNA fragment, which was made by annealing two complementary oligonucleotides LHRH-6 and LHRH-7 (Table 1) with a NdeI recognition sequence at the 5' end and a BamHI site at the 3' end to generate pYZ24-2. pYZ24 was linearized by digestion with HindIII and XhoI, and then ligated to another double-stranded tandem LHRH DNA sequence which was made by annealing oligonucleotides LHRH-8 and LHRH-9 (Table 1) with a HindIII site at the 5' end and a XhoI site at the 3' end. The resulting plasmid was designated pYZ24-3.

Figure 2:
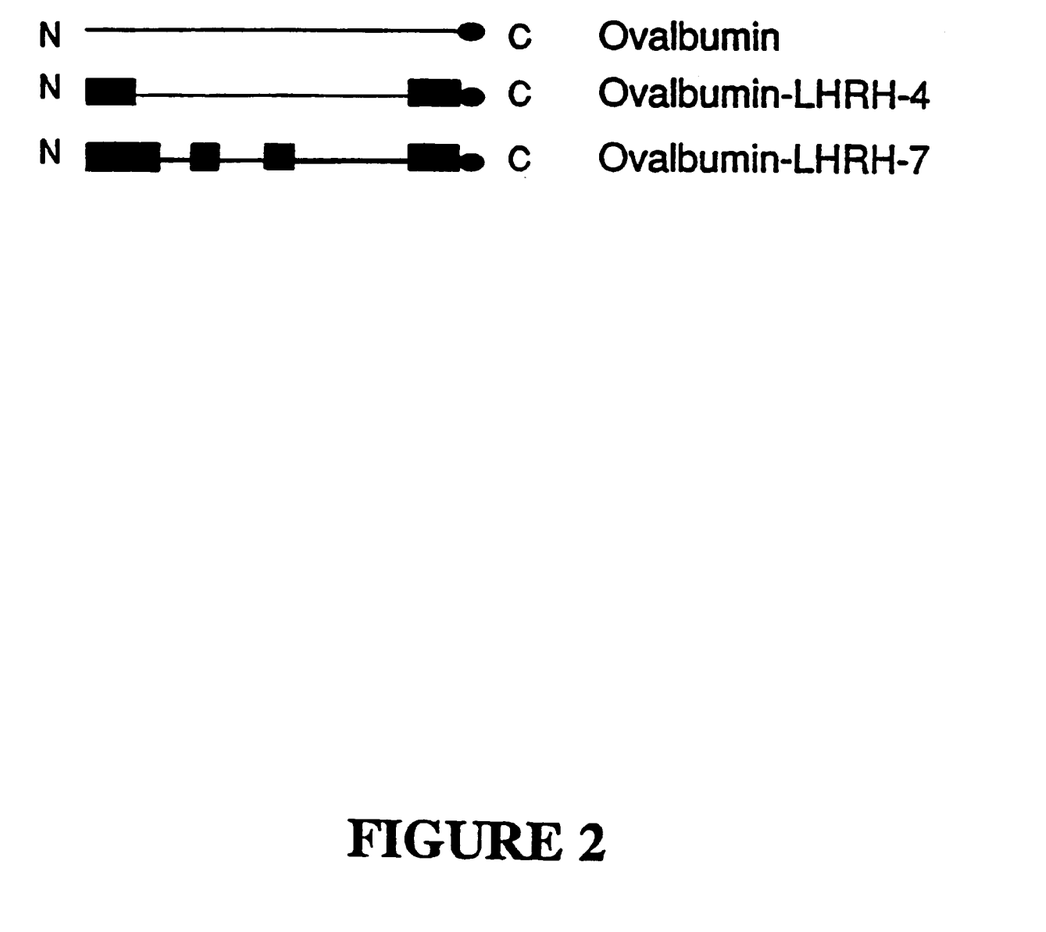

To generate pYZ24-5, pYZ24-3 was linearized by digestion with NdeI and HindIII, and then ligated with the ovalbumin fragment containing the LHRH tandem DNA sequence from the digestion of pYZ24-2 with NdeI and HindIII. To generate pYZ24-6, pYZ24-5 was linearized by digestion with BamHI and HindIII, and then ligated with the ovalbumin fragment containing 3 LHRH inserts from the digestion of pYZ24-4 with BamHI and HindIII. The structures of all of the constructed plasmids were confirmed by digestion with appropriate restriction enzymes. The structure of the ovalbumin-LHRH region of pYZ24-6 was also confirmed by complete DNA sequencing. In FIG. 2, the names of 3 plasmids are indicated on the left and the straight line represents amino acid 18–381 of ovalbumin. Open boxes represent LHRH insertion sites: Site 1 (before amino acid 18); Site 2 (between amino acid 65 and 66); Site 3 (between amino acid 97 and 98); Site 4 (immediately before Site 1); and Site 5 (immediately after amino acid 381). The solid box at the C-terminus of each protein represents the His-Tag sequence.

EXAMPLE 2

Solubility and Purification of Recombinant Ovalbumin-LHRH Proteins

The *E. coli* strains BL21 (DE3) and MV1190 were used for cloning and expressing the recombinant genes, and strain CJ236 was used for oligonucleotide-directed mutagenesis. Bacterial cells, unless otherwise indicated, were grown in Luria-Bertani medium (Sambrook et al., Molecular Cloning. Cold Spring Harbor Laboratory Press, Cold Spring Harbor, N.Y., 1989). Antibiotics were added to liquid and solid media to a final concentration of 100 $\mu$g/ml ampicillin or 50 $\mu$g/ml kanamycin, depending on the antibiotic resistance of the plasmid in the cells. Protein expression was induced by adding iso-propyl-$\beta$-D-thiogalactopyranoside (IPTG) to a final concentration of 1 mM when the cultures reached an optical density at 600 nM ($OD_{600}$) of 0.5. Cultures were then incubated in tryptone-phosphate-kanamycin medium (Moore et al., *Prot. Expres. Purif.* 4:160–163 (1993)) for an additional 3 hours at 37° C.

pET24b derivatives containing the kanamycin resistance gene express proteins under the control of the phage T7 promoter. In the T7 expression system, T7 RNA polymerase is so selective and active that almost all of the cell's resources are diverted to target gene expression (pET System Manual, 1995). Moreover, strain BL21(DE3) is deficient in both the ompT and lon proteases and thus increases expression levels of many target proteins (Studier et al., *Meth. Enzymol.* 185:60–89 (1990)).

Figure 3:
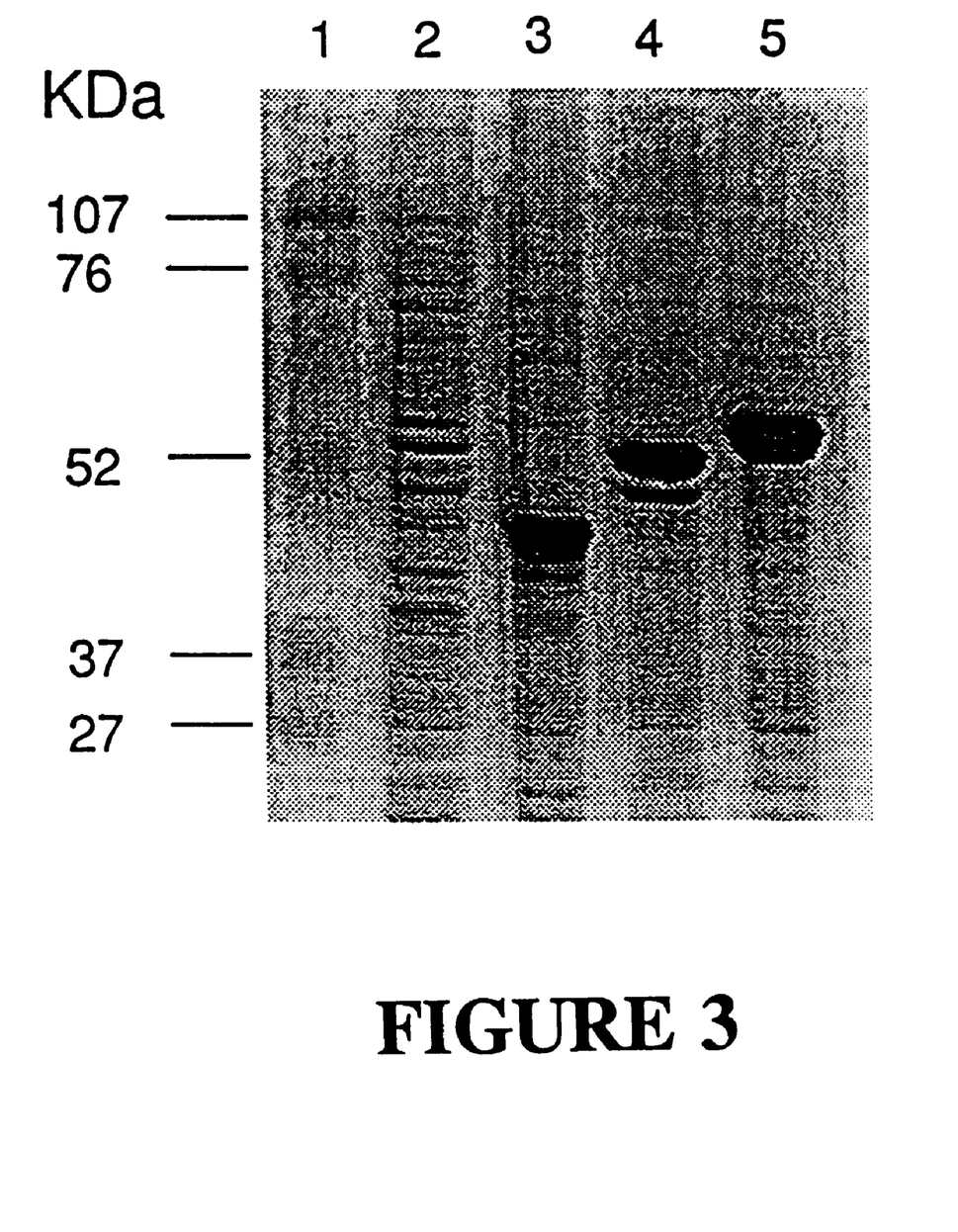

The expression of recombinant proteins ovalbumin, ovalbumin-LHRH-4 and ovalbumin-LHRH-7 is shown in FIG. 3. The whole cell proteins from induced cultures were separated by SDS-PAGE and visualized by Coomassie blue staining. Induction resulted in high level expression of recombinant ovalbumin, ovalbumin-LHRH-4 and ovalbumin LHRH-7. The protein bands which migrated at the approximate molecular weights of 40 kDa, 50 kDa and 55 kDa were highly visible in induced BL21(DE3) cells harboring plasmid pYZ24, pYZ24-5 or pYZ24-6, respectively (see FIG. 3, lanes 3–5, respectively). Lanes 1 and 2 of FIG. 3 are size markers and proteins from cells lacking expressible chimeric protein respectively.

Figure 4:
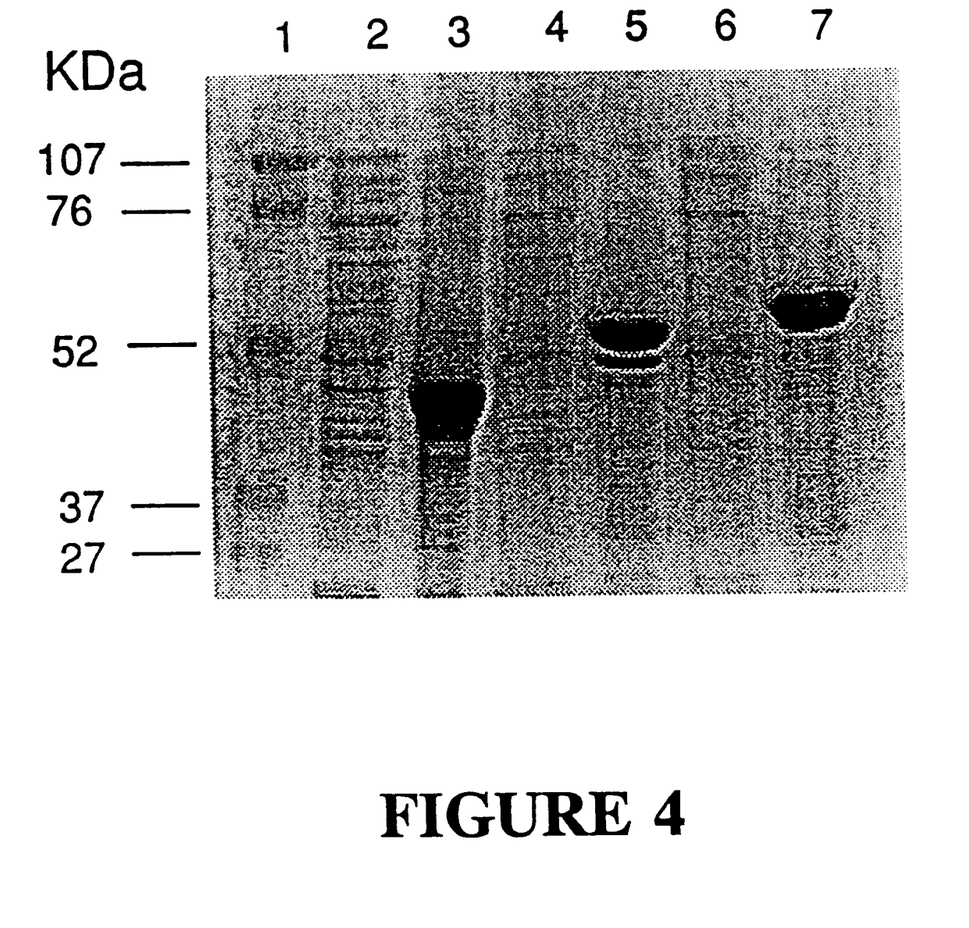
FIG. 4 shows the solubility of recombinant ovalbumin, ovalbumin-LHRH-4 and ovalbumin-LHRH-7 from plasmids pYZ24, pYZ24-5 and pYZ24-6, respectively.

A comparison of recombinant ovalbumin, ovalbumin-LHRH-4 and ovalbumin-LHRH-7 in the soluble and insoluble fractions of whole cell protein is shown in FIG. 4.

Cells were grown in tryptone-phosphate-kanamycin medium (Trp-Phos-Kan) at 37° C. for 3 hours with induction by 1 mM IPTG. Both soluble and insoluble proteins were isolated from the equivalent of 35 $\mu$l induced cultures, were separated by SDS-PAGE and were visualized by Coomassie blue staining. The gel depicted in FIG. 4 shows that nearly all the chimeric protein produced by expression of pY224, pYZ24-5 and pYZ24-6, (lanes 3, 5 and 7 respectively) was insoluble. Soluble proteins produced in cell expressing pY224, pYZ24-5 and pYZ24-6 are represented in lanes 2, 4 and 6 of FIG. 4. (Lane 1 of FIG. 4 shows size markers). Expression of the chimeric protein in different media and at lower temperatures showed the same result.

A disadvantage of insoluble proteins is that the recombinant protein does not assume a native conformation. However, these insoluble proteins have some advantages such as increased yield, protection from cytoplasmic proteases, and rapid and efficient purification (Gottesman, *Meth. Enzymol.* 185:119–129 (1990)). Moreover, such proteins may make good antigens possibly because of their persistence in the immunized animal. Harlow and Lane, Antibodies: A Laboratory Manual, Cold Spring Harbor Laboratories (1988) also found similar results with other insoluble proteins. Nonetheless, methods for solubilizing inclusion bodies are well known in the art and include such steps as solubilization in denaturing agents (such as urea, detergents, chaotropic salts) followed by renaturing the solubilized protein.

After expression of recombinant ovalbumin from pYZ24, ovalbumin with 4 LHRH inserts (ovalbumin-LHRH-4) from pYZ24-5 and ovalbumin with 7 LHRH inserts (ovalbumin-LHRH-7) from pYZ24-6 in BL2(DE3) as described above, the chimeric proteins were purified for further characterization and use. Due to their insolubility, the proteins were first solubilized in 6 M urea, centrifuged at 39,000×g for 20 min, filtered through a 0.45 $\mu$m membrane and then purified by His-Bind affinity chromatography since they contained a C-terminal His-Tag sequence. When present at the C-terminus of the target protein, this sequence serves as an affinity tag for affinity purification on Ni-chelation columns (pET System Manual, Novagen, 1994).

Figure 5:
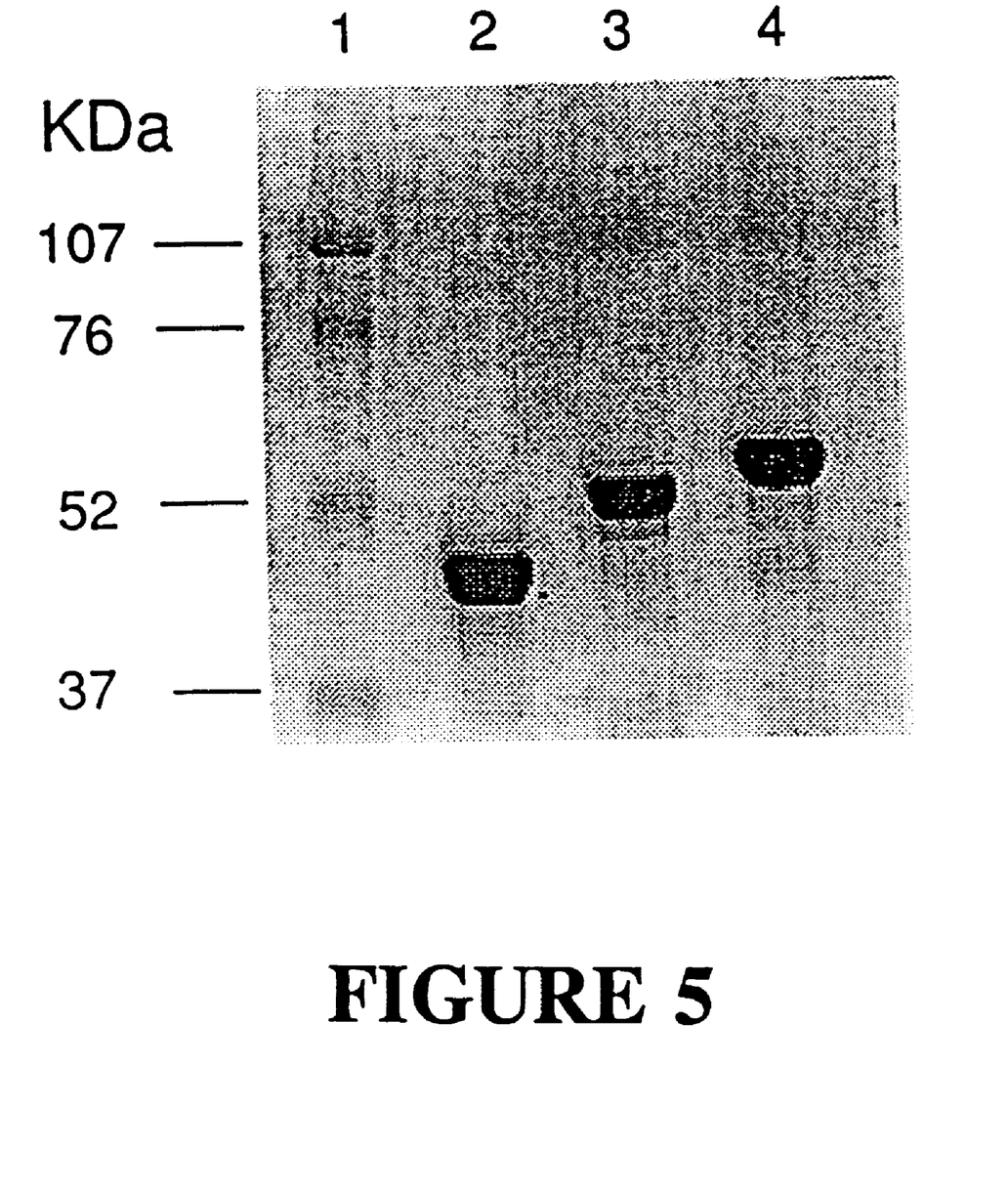
FIG. 5 illustrates the purification of recombinant ovalbumin, ovalbumin-LHRH-4 and ovalbumin-LHRH-7 by His-Bind affinity chromatography.

More specifically, the pET24b derivatives contain a run of six histidine codons which are linked in-frame to the 3' ends of the ovalbumin-LHRH DNA. When expressed as the C-terminus of the target protein, this sequence serves as an affinity tag for affinity purification. Because of their insolubility, purification of ovalbumin, ovalbumin-LHRH-4 and ovalbumin-LHRH-7 was performed under denaturing (6M urea) conditions. Purified recombinant proteins are shown in FIG. 5 which depicts SDS-PAGE analysis of the proteins as visualized by Coomassie blue staining. Lane 2 of FIG. 5 shows purified ovalbumin, lane 3 shows purified ovalbumin-LHRH-4 and lane 4 shows purified ovalbumin-LHRH-7. The proteins were then eluted from the gel, precipitated with 3 volumes of acetone, resuspended in saline and mixed with an adjuvant before vaccination. In other cases, proteins were solubilized in urea and mixed with an adjuvant before vaccination. (See below).

EXAMPLE 3

Vaccination of Mice With Chimenic Ovalbumin-LHRH

Each of the three recombinant proteins ovalbumin, ovalbumin-LHRH-4 and ovalbumin-LHRH-7 (precipitated with acetone as described above and resuspended at 1 $\mu$g/$\mu$l in physiological saline) was mixed with an equal volume of complete Freund's adjuvant (CFA). The mixture was emulsified until a stable water-in-oil emulsion was obtained, 50 μg of protein per 100 μl of emulsion was used per injection.

Seventeen female 7-week old BALB/c mice were randomly divided into three groups. Treatment I (control, n=6), Treatment II (n=5) and Treatment III (n =6) mice were injected with ovalbumin, ovalbumin-LHRH-4 and ovalbumin-LHRH-7, respectively. One primary immunization at the base of the tail (subcutaneous) using CFA was followed by one booster in the back of the neck using Incomplete Freund's Adjuvant (IFA) 3 weeks later. Mice were killed 2 weeks after the booster. The reproductive tracts (uteri+ovaries) were weighed. Serum anti-LHRH antibody titers were measured by an enzyme-linked immunoadsorbent assay (ELISA). Briefly, LHRH (BACHEM, CA) was coated onto amine-binding microtiter plates (COSTAR), which were allowed to react with dilutions of the mouse sera. After extensive washing, anti-LHRH antibodies were detected with goat-anti-mouse IgG coupled to horseradish peroxidase. The formation of color in each well was photometrically quantified using a computerized plate reader (490 nm wavelength). Titers were defined as the maximal serum dilution capable of forming color that was 2-fold greater than pre-immune mouse serum at the same dilution.

Vaccination of female mice with either purified ovalbumin-LHRH-4 (Treatment II) or ovalbumin-LHRH-7 (Treatment III) elicited anti-LHRH titers. The average titer was highest in Treatment III (ovalbumin-LHRH-7). Treatment III decreased ($P<0.01$) uterine-ovarian weight (89±11) vs Treatment I (138±6 mg) and Treatment II (126 mg±16 mg). Ovalbumin-LHRH-4 induced lower anti-LHRH antibody production (Table 2) than ovalbumin-LHRH-7, and one out of five mice did not show an anti-LHRH titer at the lowest dilution tested (1:100).

TABLE 2

Evaluation of Antigenicity of Recombinant Ovalbumin-LHRH Proteins

| Treatment | anti-LHRH titer (mean ± SE) | Uterine-ovarian weight (mg) (mean ± SE) (n) |
|---|---|---|
| I (ovalbumin) | —[a] | 138 ± 6 (6) |
| II (ovalbumin-LHRH-4) | 90 ± 33 | 126 ± 16 (5) |
| III (ovalbumin-LHRH-7) | 733 ± 344 | 89 ± 11** (6) |

**Different from control, $P < 0.01$.
[a]No anti-LHRH titer.

All of the mice in Treatment III showed anti-LHRH titers, but one of them did not have a reduced uterine-ovarian weight compared to the mean uterine-ovarian weight in control mice. The linear regression between the weight of the reproductive tract (Y) and the serum anti-LHRH titer (X) was Y=108.2710–0.0261 X, the correlation coefficient r=−0.79, ($P<0.05$). Mean anti-LHRH titers in Treatment III fit the biological effect well (Table 2).

EXAMPLE 4

Vaccination of Mice with Chimeric Proteins and Alternative Adjuvants

The chimeric ovalbumin-LHRH-7 protein was determined to be the most immunogenic protein used in Example 3. To further investigate its immunogenicity, adjuvants Zmax™ (Zonagen, Inc., The Woodlands, Tex.) and Immumax™ (Zonagen, Inc.) were used with two different doses of ovalbumin-LHRH-7. Seventy female 6–8 week BALB/c mice were randomly divided into seven groups of 10 mice each. Group 1 was used as unimmunized controls (UC). Each of the mice in group 2, 3, 4, 5, 6 and 7 was immunized with 30 μg of ovalbumin in Zmax™ adjuvant (O30/Zmax™), 10 μg of ovalbumin-LHRH-7 (urea solubilized) in Zmax™ (OL10/Zmax™), 30 μg of ovalbumin-LHRH-7 (urea solubilized) in Zmax™ (OL30/Zmax), 30 μg of ovalbumin in Immumax (O30/Immumax™), 10 μg of ovalbumin-LHRH-7 (acetone precipitated and resuspended in physiological saline) in Immumax™ (OL10/Immumax™) and 30 μg of ovalbumin-LHRH-7 (acetone precipitated and resuspended in physiological saline) in Immumax™ (OL30/Immumax™), respectively. Three immunizations were given at 4-week intervals. Mice were bled by cardiac puncture and sacrificed 2 weeks after the third immunization. The uterus and ovaries were removed and weighed. Serum anti-LHRH titers were measured by ELISA as described above.

Anti-LHRH titers were detected in all of the ovalbumin-LHRH-7-immunized mice, regardless of the dose at 10 μg or 30 μg per immunization per mouse. However, variations in anti-LHRH titers were shown between mice (Table 3). Significant decreases were found in the uterine-ovarian weight following immunization with 30 μg of ovalbumin-LHRH-7 (OL30/Zmax) ($P<0.005$) and 10 μg of ovalbumin-LHRH-7 (OL10/Immumax) ($P<0.025$), respectively (Table 3).

TABLE 3

Evaluation of Effectiveness of the Recombinant Ovalbumin-LHRH-7 Using Zmax ™ and Immumax ™ Adjuvants.

| Group | Treatment | Anti-LHRH titer (mean ± SE) | Uterine-Ovarian Weight (mg) (mean ± SE) (n)[b] |
|---|---|---|---|
| 1 | none | —[a] | 95 ± 9 (9) |
| 2 | O30/Zmax ™ | — | 100 ± 8 (4) |
| 3 | OL10/Zmax ™ | 348 ± 243 | 40 ± 12*** (10) |
| 4 | OL30/Zmax ™ | 349 ± 269 | 89 ± 21 (3) |
| 5 | O30/Immumax ™ | — | 82 ± 8 (9) |
| 6 | OL10/Immumax ™ | 164 ± 1230 | 88 ± 13 (10) |
| 7 | OL30/Immumax ™ | 500 ± 231 | 50 ± 11* (10) |

***$P < 0.005$
$P < 0.025$
[a]No anti-LHRH-titer
[b]Each group started with 10 mice. However, some died before the experiment was completed.

The tests for the linear regression and correlation coefficient between the weight of reproductive tracts and anti-LHRH titers were analyzed by the procedure described by Ott, "An introduction to statistical methods and data analysis." 4th Edition. Belmont, Calif., (1993). The difference in weight of reproductive tracts was analyzed using the ANOVA procedure for a completely randomized design, and the significance of treatment effects was determined using Fisher's Least significance (LSD) test (Gill, "Design and analysis of experiments in the Animal and Medical Sciences." Iowa State University Press, Ames, IA. (1978)

EXAMPLE 5

Vaccination of Heifers with Recombinant Ovalbumin-LHRH-7

Eight crossbred heifers were randomly assigned to two treatment groups. Cyclicity was determined for all heifers prior to immunization by analysis of serum progesterone concentrations. Treatments consisted of recombinant ovalbumin (control) and ovalbumin-LHRH-7. Zmax™ (Zonagen, Inc.) was used as an adjuvant for both treatments. One primary and two booster immunizations were administered at five week intervals. All injections were administered into the mammary gland.

Figure 6:
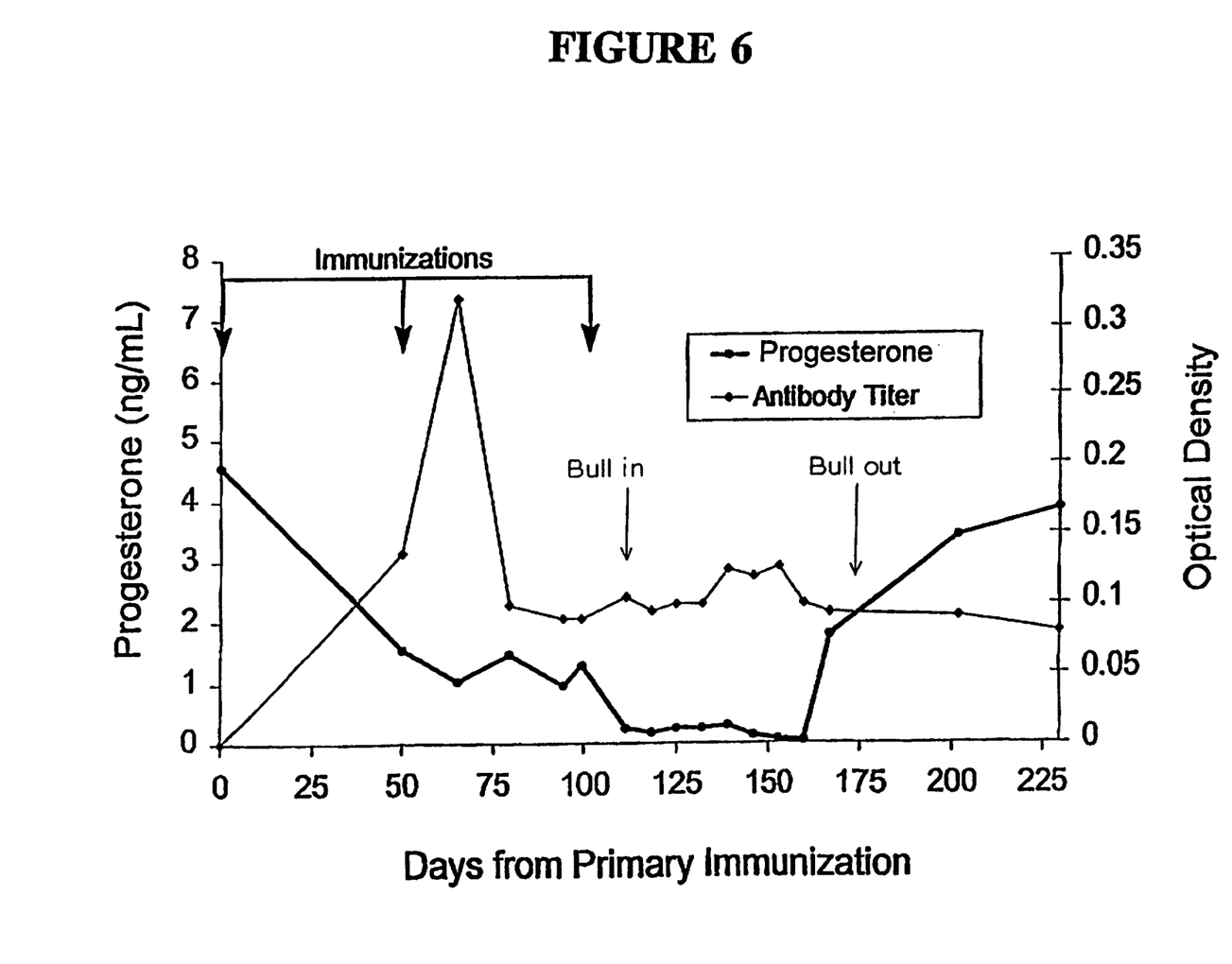
FIG. 6 shows serum progesterone (P4) levels from heifers treated with an ovalbumin-LHRH-7 sterilization vaccine and antibody titers against ovalbumin-LHRH-7.
Figure 7:
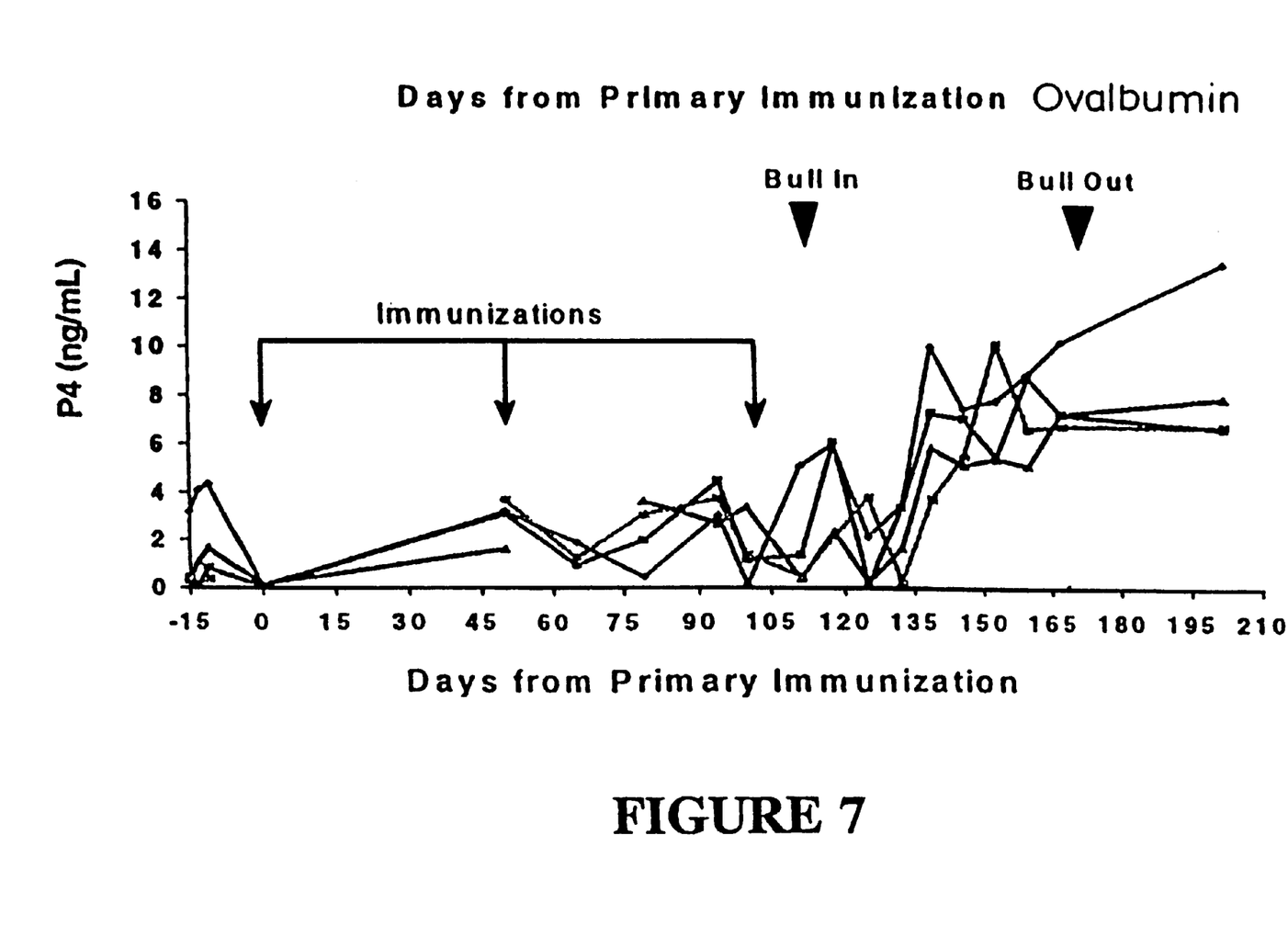
FIG. 7 shows serum progesterone (P4) levels from control heifers treated with ovalbumin.

Blood samples were taken biweekly between the second and third immunizations and weekly after that to determine serum progesterone concentrations and anti-LHRH antibody titers. Serum progesterone concentrations (<1ng/mL) the four ovalbumin-LHRH-7 treated heifers were suppressed for a time period of about 60–123 days (see FIG. 6, illustrating mean progesterone levels and mean antibody titers) and the animals stopped cycling between about days 110–160. All of the control heifers (immunized with ovalbumin) continued cycling throughout the trial. (See FIG. 7).

Antibody titers against ovalbumin-LHRH-7 were also measured by ELISA as described above and were shown to peak in the immunized heifers shortly after the second immunization after which titers decreased. (See FIG. 6).

On Day 111 after the primary immunization, a bull was placed with all heifers for 60 days to compare fertility of the two groups. All of the control heifers (immunized with ovalbumin) became pregnant within 21 days of the time the bull was placed with the heifers. Heifers immunized with ovalbumin-LHRH-7 were infertile for the time period in which ovulation was suppressed. However, infertility was reversible since two heifers immunized with ovalbumin-LHRH-7 eventually became pregnant. The restoration of fertility in the vaccinated heifers (ovalbumin-LHRH-7) was also accompanied by a decrease in antibody titer against the chimeric protein.

The foregoing was presented by way of illustration and is not intended to limit the scope of the invention as set out in the appended claims. All references cited are incorporated herein by reference.

We claim:

1. A method of inducing infertility in a mammal, the method comprising administering to the mammal a contraceptively effective dose of a recombinant chimeric protein in a pharmaceutically acceptable diluent, adjuvant or carrier, said chimeric protein consisting essentially of ovalbumin or a fragment thereof and a reproduction related polypeptide or fragment or fragments thereof, wherein said reproduction related polypeptide is inserted within an antigenic region of said ovalbumin or fragment thereof.

2. The method of claim 1 wherein the reproduction related polypeptide is luteinizing hormone releasing hormone (LHRH) or a fragment thereof.

3. The methond according to claims 1 or 2 wherein the chimeric protein comprises two or more reproduction related polypeptides or fragment or fragments thereof.

4. The method of claim 1 wherein the reproduction related polypeptide is selected from the group consisting of follicle-simulating hormone (FSH), luteinizing hormone (LH), and fragments thereof.

* * * * *

UNITED STATES PATENT AND TRADEMARK OFFICE
CERTIFICATE OF CORRECTION

PATENT NO.        : 6,045,799
APPLICATION NO. : 09/072508
DATED             : April 4, 2000
INVENTOR(S)       : Reeves et al.

Page 1 of 1

It is certified that error appears in the above-identified patent and that said Letters Patent is hereby corrected as shown below:

Column 1, line 7, "9401624" should be --94-37203-0794--.

Signed and Sealed this

Seventeenth Day of November, 2009

David J. Kappos
*Director of the United States Patent and Trademark Office*